(12) United States Patent
Eggler

(10) Patent No.: US 6,758,670 B2
(45) Date of Patent: Jul. 6, 2004

(54) DENTAL SET PLATES

(75) Inventor: Andreas Eggler, Wolfurt (AT)

(73) Assignee: Ivoclar Vivadent AG, Schaan (LI)

(*) Notice: Subject to any disclaimer, the term of this patent is extended or adjusted under 35 U.S.C. 154(b) by 33 days.

(21) Appl. No.: 10/059,655

(22) Filed: Jan. 29, 2002

(65) Prior Publication Data

US 2002/0137000 A1 Sep. 26, 2002

Related U.S. Application Data

(60) Provisional application No. 60/287,774, filed on Apr. 1, 2001.

(30) Foreign Application Priority Data

Mar. 23, 2001 (DE) ......................................... 101 14 210

(51) Int. Cl.[7] .............................................. A61C 19/10
(52) U.S. Cl. .......................................... 433/26; 206/83
(58) Field of Search .......................... 433/26; 206/63.5, 206/83, 368, 369

(56) References Cited

U.S. PATENT DOCUMENTS

| 2,318,618 A | * | 5/1943 | Myerson et al. | 206/83 |
|---|---|---|---|---|
| 2,341,153 A | | 2/1944 | Myerson | 433/26 |
| 2,874,487 A | | 2/1959 | Bloom et al. | 206/232 |
| 3,783,996 A | * | 1/1974 | Gerard et al. | 206/17.5 |
| 4,775,318 A | * | 10/1988 | Breslin | 433/26 |
| 5,782,632 A | | 7/1998 | Foser | 433/26 |
| 6,079,981 A | | 6/2000 | Sekendur | 433/171 |
| 6,415,916 B1 | | 7/2002 | Rini | 206/83 |

FOREIGN PATENT DOCUMENTS

| DE | 7411122 U | 7/1974 |
|---|---|---|
| EP | 0 827 720 A2 | 3/1998 |

* cited by examiner

*Primary Examiner*—John J. Wilson
(74) *Attorney, Agent, or Firm*—John C. Thompson; Alan S. Korman

(57) ABSTRACT

A dental set plate for supporting therein a set of replacement teeth includes a support body having a channel and a deformable mass disposed in the channel of the support body for releasably adhesively retaining a row of replacement teeth pressed thereinto. The dental set plate also includes a non-opaque hood covering the support body and the replacement teeth supported on the support body and product information indicia affixed to the hood. The dental set plate is dimensioned for stocking of the dental set plate in an index structure which retains dental set plates and the walls of the hood have an extent such that the walls terminate within the index structure in which the dental set plate is stocked.

15 Claims, 3 Drawing Sheets

DENTAL SET PLATES

CROSS-REFERENCE TO RELATED APPLICATIONS

This application claims foreign priority benefits under 35 U.S.C. § 119 (a)–(d) from German patent application ser. no. 101 14 210.2 filed Mar. 23, 2001. In addition, this application claims the benefit under 35 U.S.C. § 119(e) of U.S. provisional patent application Ser. No. 60/287,774 filed Apr. 1, 2001

BACKGROUND OF THE INVENTION

The present invention relates to a dental set plate.

Dental set plates have long been known such as, for example, the dental set plate described in DE-GM 7 411 122. The dental set plate described in that publication retains as a dental set six or seven front teeth or side teeth in a row in readiness for a dentist or a dental technician. The dentist makes use of drawers with inserts in an index or classification structure which permit the arrangement of a plurality of such dental sets in one over another or side-by-side relationship. In this manner, a quick pre-selection can be undertaken of the color and form of a replacement tooth which is to be made available. The support body includes a receiving channel for receiving therein a wax-like mass into which the replacement teeth can be pressed. At the same time, adequate writing space above and below the receiving channel is available, whereby the tooth color and form, the tooth fabricator, and further individual details can be recorded in abbreviated form.

Dental sets of such teeth are supplied in finished condition in the dental set plates. In this regard, special transport containers have been designed which support the dental set plates for transport in one over another and side-by-side relationship to one another. The cases serving as these transport containers are opened by the dentist or the dental office staff and sorted out into the drawers. This process is a determinedly time consuming logistical process as the placement and removal of the dental set plates must each be noted.

It continually occurs in the transport of the transport cases that individual teeth come loose and cannot thereafter be restored to the correct dental set plate without considerable effort. This evidently occurs in particular if the dental set plates have been transported during particularly cool conditions. The lowering of the transport temperature results in a hardening of the deformable mass into which the teeth have been pressed, as in most instances the deformable mass is comprised of wax or a wax derivative, whereupon the retention capability of the mass is substantially reduced.

To improve the retention capability of the mass, it is known to use a binder wax which exhibits a good retention capability even at significantly lower temperatures. The use of a binder wax permits transport and storage down to minus 10° C. without dislodgment of the transported teeth. However, the binder wax has the undesirable property that it has a distinctly viscous-sticky characteristic at room temperature. In practice, it is difficult if not impossible to remove the remnants of the binder wax from the teeth; at the same time, the danger exists that the binder wax remnants detract from the restoration result.

There is a further problem with conventional dental set plates with regard to the color variations of different batches even from the same fabricator. Differences in color and light transmissivity occur in different batches even with respect to teeth of the same color and light transmissivity properties. In order to obtain the greatest possible uniformity in the restoration result, it is desirable to use only those teeth fabricated from the same batch so that color and light transmissivity uniformity can be achieved. With conventional dental set plates, however, it is not possible to regularly establish the batch origin of the teeth.

It would further be desirable to be able to ascertain, in connection with the never ending warranty events or damage to teeth, individual information concerning the transport of the dental set plates. At the same time, it is currently unsatisfactory that the stockage must be individually manually controlled. Such control is decidedly resource demanding in that those assigned to the task must very precisely grasp the dental set plates on hand and then perform the corresponding inventory control. An error in the manual inventory control easily leads to delivery bottlenecks so that, in the event, a poorly suited tooth replacement may have to be used if, due to inadvertence, a more suitable replacement tooth has not been re-ordered. Moreover, the manual inventory control is labor intensive and is thus not desirable from a cost control perspective.

It has been proposed to provide bar codes on the underside of the dental set plates to thereby enable automatic data gathering. However, the affixation of such bar codes on the underside of the dental set plates would require removal and turning movement of the underside to effect a reading of the bar code by a bar code reader during a data gathering step.

SUMMARY OF THE INVENTION

The present invention offers a dental set plate as a solution to the challenge of providing a dental set plate which permits an optimally reduced color variation between the replacement teeth and the teeth to be replaced while at the same time improving the storage and transport dispositions without having to forego the already on hand storage location for such dental set plates with its index or classification arrangement.

In accordance with the present invention, it is particularly advantageous if the hood offers the possibility of protecting the teeth during their transport so that the danger of individual teeth getting lost, and thus rendering the dental set basically useless, is foreclosed, as well as also offering the possibility to provide identification of the dental set so that, at the least, the individual sorting out of the dental sets is facilitated. The dental set plate of the present invention unexpectedly provides the possibility of configuring the deformable wax-like mass with a less sticky consistency without the danger of loss of the retained dental items. If the replacement teeth are maintained in inventory by the dentist or the dental technical personnel, the dental set plates are typically at room temperature whereupon the wax-like mass, in any event, better retains the replacement teeth within the dental set plate. At the same time, the shaking experienced by the dental set plates in their stocked dispositions within drawers is less than the shaking which can occur during the transport of the dental set plates. The transport of the dental set plates also brings forth the danger that the dental set plates will be turned around. The see through hood of the dental set plate of the present invention also aids in preventing such turning around of the dental set plates during their transport. As a consequence of the ability to provide a retaining mass having relatively less stickiness, the risk is reduced that remnants of the retaining mass will adhere to the teeth which are removed from their retained dispositions on the mass and thereby lead to unclean dental conditions.

In accordance with the present invention, it is, in addition, particularly advantageous if the dental set plates are stackable and can thereby be automatically transported and stocked.

It is especially advantageous, in accordance with the present invention, if the hood of the dental set plate remains with the on hand index or classification structure for stocking the dental set plates. In this connection, it is provided that the dimensions of the support body are, at least in the region thereof into which the walls of the hood extend, configured at a smaller dimension and, in fact, configured in correspondence with the wall strength of the hood. In one embodiment of the dental set plate of the present invention, the hood is disposed under the support body on a step or offset so that a certain sealing mechanism is formed thereat. This embodiment of the dental set plate is particularly advantageous if it is sought to also provide protection of the replacement teeth against unclean or unhygienic elements.

The drawers of a dental teeth sample cabinet are typically constructed so as to offer a certain sealing off against the entry of dust and dirt deposition. Nonetheless, conventional dental set plates stocked in such cabinets must undergo a cleaning from time to time which proves itself to be decidedly laborious as a straight forward vacuuming of the replacement teeth with a vacuum can lead to a loss of the teeth. The hood of the dental set plate of the present invention, on the other hand, drastically reduces the infiltration of dust and debris even during a stockage of the replacement teeth for several years. It is preferred, in this connection, that the hood cover or close off the support body on all sides thereof.

In another embodiment of the dental set plate of the present invention, each wall of the support body to which a wall of the hood extends, extends directly downwardly. This configuration permits a turning over of the hood so that the inverted hood extends over the support body from below.

The product information indicia provided on the dental set plate in accordance with the present invention, if disposed on a side of the dental set plate such as, in particular, on a side wall of the hood, can be readily noted and, as well, can be readily accessed by a bar code reader or scanner. In this manner, the stockage of the dental set plates in a dental laboratory, a dental supply location, and a dentist office can be accomplished in an automatic manner. In this connection, there exists, for example, the possibility to briefly guide new dental set plates over the scanner during the stockage of such dental set plates in order to thereby maintain and update an inventory accounting. A corresponding inventory accounting program permits the inventory status to be determined at all times. If a replacement tooth is used, the corresponding dental set plate including its hood is guided over another scanner or the one scanner is switched into a mode in which it captures information to indicate the removal of the replacement tooth. In this manner, the status of the stockage of the dental set plates can be precisely tracked by machine and it is also possible to set up an automatic reordering capability which is triggered when the available supply drops below a predetermined minimum stockage amount.

The product information indicia on the dental set plate of the present invention also permits identification of the batch from which the dental set in the dental set plate was fabricated as well as provides the ability to trace the fabricator of the dental set.

The dental set plate of the present invention permits the realization of at least one see through region through which the replacement teeth can be readily viewed. The hood of the dental set plate can, for example, be comprised of polyacrylic or another desired suitable material. If a particularly clear plastic or synthetic material without color distortion is used, it is also possible to perform a color evaluation without the risk that the hood will cause a color distortion.

In an advantageous embodiment of the dental set plate of the present invention, two grip areas are provided on the support body each of which is configured with a groove, corrugation, or depression. The side walls of the hood extend preferably backwardly at the grip areas so that the opening of the dental set plate can be reliably and quickly performed while a firm seating of the hood is nonetheless ensured to thereby contribute to a good seal against the penetration into the dental set plate of dirt and other outside elements as well as preventing a loss of the replacement teeth from the dental set plate during its transport.

The product information indicia can be affixed to a side wall or end wall of the hood. In those locations, there is sufficient unused space so that, for example, a decidedly large bar code can be affixed. In one embodiment of the dental set plate of the present invention, the product information indicia is affixed to the cover surface of the hood along an edge. In this manner, unobstructed viewing of the writing on the support body and on the replacement teeth themselves is possible. Nonetheless, the product information indicia can as needed for the purpose, for example, of inventory accounting, also be readable by a hand scanner if the dental set plate is disposed in the drawer of the dental teeth sample cabinet, as the side wall of the dental set plate is typically covered due to the serial one after another arrangement of the dental set plates with one another in the cabinet.

In accordance with the present invention, it is especially advantageous if the dental set plates with their hoods are stackable and thereby accessible for an automatic retrieval.

The affixation of the product information indicia on the side walls of the dental set plates permits the capture of product information to also be performed in a stacked disposition of the dental set plates. It is to be understood that the product information indicia can be disposed as needed on the front side as well as the backside of the dental set plate.

In a further advantageous embodiment of the dental set plate of the present invention, a tamper indication element is provided. This element can be in the form, for example, of an adhesive strip secured to the hood and the support body whose unbroken condition can be taken as a guarantee that the dental set plate has not been opened.

In an additional advantageous embodiment of the dental set plate of the present invention, the tamper indication element is in the form of an adhesive strip having product information indicia thereon so that a single label can ensure the securement of the hood and the support body to one another as well as provide the product information indicia.

DETAILED DESCRIPTION OF THE PREFERRED EMBODIMENT

Figure 1:
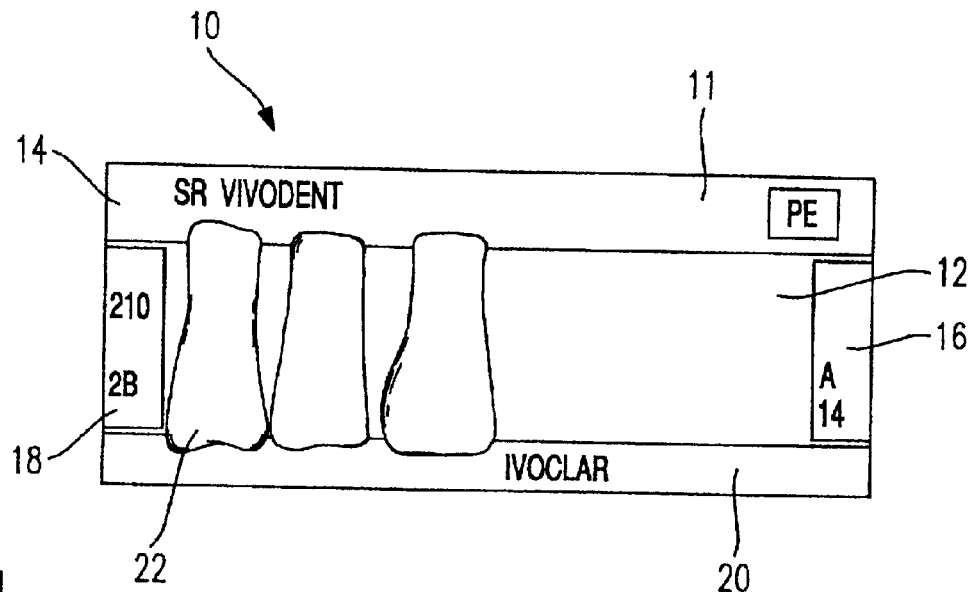
FIG. 1 is a top plan view of one embodiment of the dental set plate of the present invention shown without the hood thereof and showing the support body.

FIG. 1 shows one embodiment of the dental set plate of the present invention, designated as the dental set place 10. The dental set plate 10 includes a support body 11 which is conventionally configured with a channel. The support body 11 includes a receipt locution for receiving therein a wax-like, in particular, a plastically deformable mass 12. Front and rear sides of the dental set plate are provided with upper surfaces 14 and 20 of which extend above and below the mass 12 which are written upon in suitable manner with information, such as, for example, the name of the dental fabricators, the type of teeth, and the dental material.

The sides of the interior of the support body 11 are bound by inserts 16 and 18 which display further information with respect to the teeth form and color.

In the embodiment illustrated in FIG. 1, the mass 12 is configured as a band which extends transversely across the support body 11. It is to be understood that, in a modified embodiment of the dental set plate, a cradle-type receiver for the mass 12 can alternatively be provided.

Six or eight teeth 22 are pressed into the mass 12. The teeth partially overlap the surfaces 14 and 20 but in a limited manner such that the writing on the surfaces can be viewed in an unobstructed manner.

Figure 2:
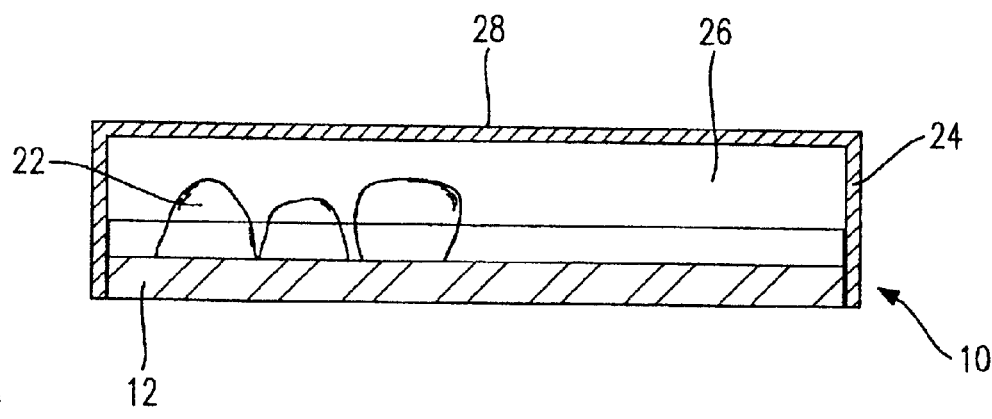
FIG. 2 is a longitudinal side elevational view of the one embodiment of the dental set plate of the present invention shown in FIG. 1.

FIG. 2 shows detail of how a hood 24 can be mounted on the support body 11. The hood 24 is comprised of a see through material and covers five sides of the support body. The hood forms a hollow space 26 in which the teeth 22 are laid out. The height of the hollow space 26 is selected such that even the largest of the teeth 22 to be retained can be accommodated with clearance. With the hood 24 in its seated position thereon, the dental set plate 10 has a parallelepiped shape.

In connection with the one embodiment of the dental set plate of the present invention shown in FIG. 1, it is presumed that an index or classification frame structure is available at the storage site of the dental set plate so that dental cabinets which are already on hand therewith can be readily outfitted with the dental set plates of the present invention. In this regard, the dimensions of the support body 11 on its four sides are reduced in correspondence with the wall strength of the hood 24.

Figure 3:
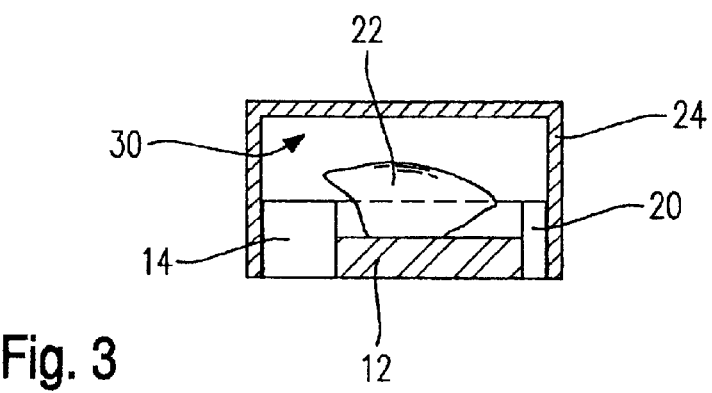
FIG. 3 is a lateral side elevational view of the one embodiment of the dental set plate of the present invention shown in FIG. 1.

FIG. 3 shows the manner in which the teeth 22 can be disposed on the mass 12. Following removal of the hood 24, a tooth or teeth can be readily removed due to the forward overlapping of the teeth relative to the surface 14.

In a modified embodiment of the dental set plate of the present invention, the ends 30 and 30a are open, as seen in FIG. 3, so that the hood 24 extends over only three sides of the support body 11.

Figure 4:
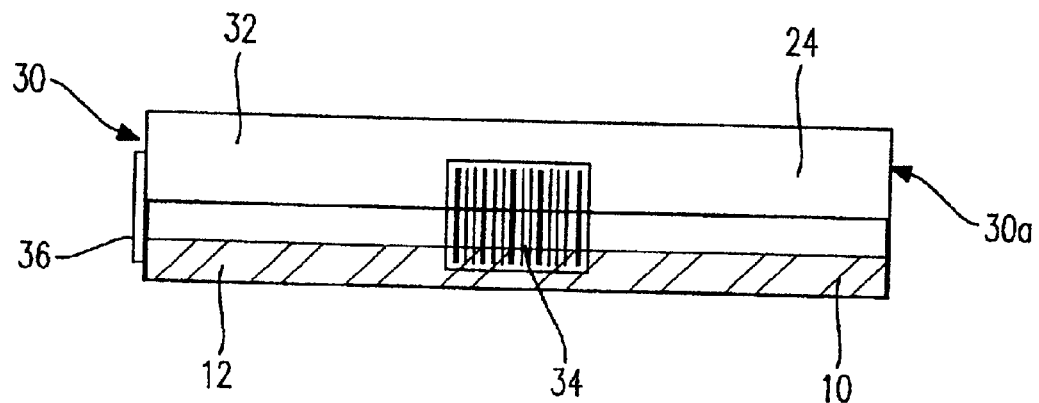
FIG. 4 is a front elevational view of another embodiment of the dental set plate of the present invention showing a product information code on the hood

FIG. 4 illustrates one manner in which product information indicia can be affixed to the dental set plate. Two product information indicia 34 and 36 are shown although it is to be understood that alternatively a single one of the product information indicia can be provided. The side wall 32 of the hood, in any event, offers sufficient place for receiving thereon, for example, a bar code.

Figure 5:
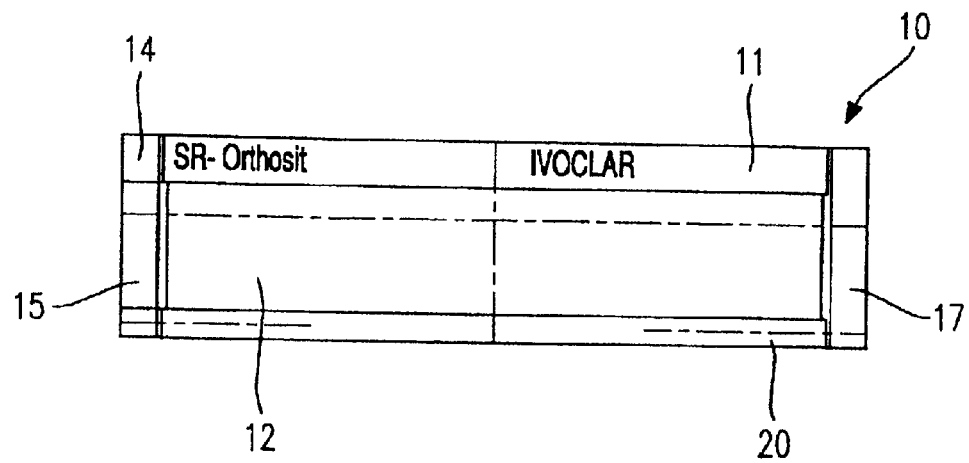
FIG. 5 is a top plan view of a further embodiment of the dental set plate of the present invention shown without the hood thereof.
Figure 6:
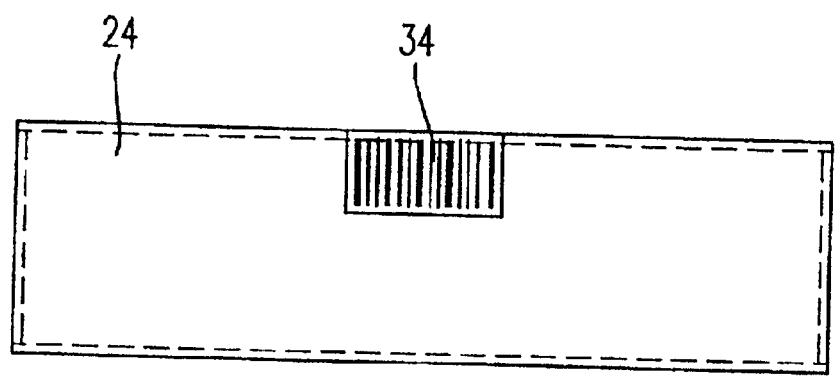
FIG. 6 is a top plan view of the hood of the further embodiment of the dental set plate of the present invention shown in FIG. 5.

It is also possible to provide product information indicia in label form on the top side 28 of the hood 24. This can be seen, for example, in the variation of the support body 11 shown in FIG. 5. In this variation of the support body, the mass 12 is supported in a cradle, which, in lieu of the inserts 16 and 18, has side walls 15 and 17. In this variation, adequate blank space for writing is available in the middle of the top surface 14. This permits the affixation of product information indicia 34, as seen in FIG. 6, at a location which overlaps this blank space. Even if the product information indicia 34 is not in see through form, a view of the teeth or the other information on the surfaces 14 and 20 can still be gained.

It is to be understood that the affixation of the product information indicia 34 can be accomplished in accordance with the preferences of the user and several product information indicia can be provided as needed.

Figure 7:
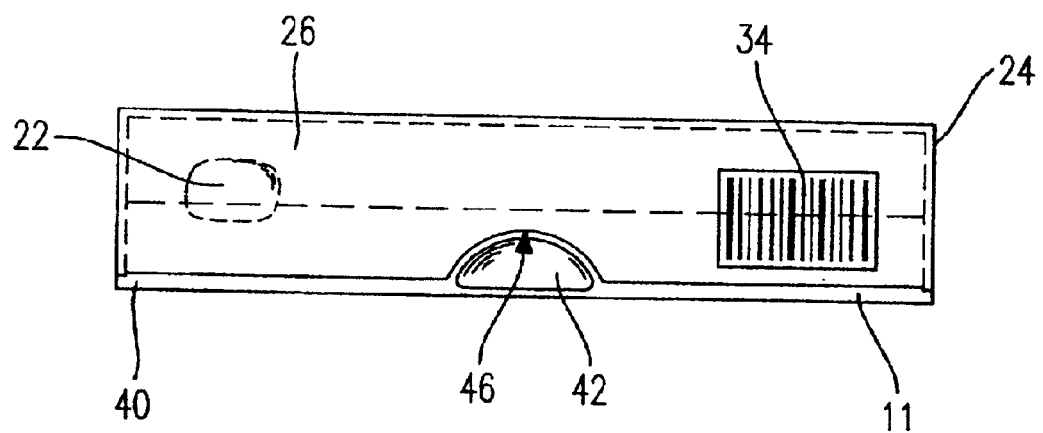
FIG. 7 is a side elevational view of an additional embodiment of the dental set plate of the present invention.

A modified embodiment of the dental set plate of the present invention is shown in FIG. 7. In this embodiment, a projection or flange 40 extends around the lower portion of the support body 11. The hood 24 extends in this embodiment of the dental set plate until reaching the projection 40 but does not extend outwardly of the support body 11. This embodiment of the dental set plate permits a particularly good sealing off of the hollow space 26 to ensure dust free receipt therein of the teeth 22. This embodiment of the dental set plate is characterized by a grip recess 42 formed on a side surface of the support body 11 and aligned with a corresponding cut out 46 in the hood. The grip recess 42 enables the hood and the dental set plate to be easily separated from one another.

The present invention is, of course, in no way restricted to the specific disclosure of the specification and drawings, but also encompasses any modifications within the scope of the appended claims.

What is claimed is:

1. A dental set plate assembly for supporting therein a set of replacement teeth, comprising:

a support body having substantially planar front and back sides and transversely spaced apart sides which, with the front and back sides, define a planar transversely extending quadrilateral deformable mass receiving elongated channel, the sides having upper surfaces which are written upon in a suitable manner;

a quadrilateral deformable mass disposed in the channel of the support body, the deformable mass releasably adhesively retaining an elongated row of replacement teeth pressed thereinto;

a non-opaque hood mounted directly upon the support body for covering the replacement teeth retained by the deformable mass carried by the support body, the hood having at least one see through region on the top side thereof through which the replacement teeth can be readily viewed, the support body and hood having a parallelepiped shape; and product information indicia affixed to the hood.

2. A dental set plate assembly according to claim 1, wherein the product information indicia is affixed to the hood on at least one or an end wall and a side wail thereof.

3. A dental set plate assembly according to claim 1, wherein the dental set plate assembly is dimensioned for stocking of the dental set plate assembly in an index structure which retains dental set plate assemblies and the walls of the hood have an extent such that the walls terminate within the index structure in which the dental set plate assembly is stocked.

4. A dental set plate assembly according to claim 1 and further comprising a tamper indication element extending to and between the hood and the support body.

5. A dental set place assembly according to claim 4, wherein the tamper indication element is an adhesive strip which at least partially encircles the support body and the hood.

6. A dental set plate assembly according to claim 4, wherein the product information indicia is affixed to the tamper indication element.

7. A dental set plate assembly according to claim 1, wherein the product information indicia is in the form of a selected one of an imprint on the hood and a label affixed to the hood.

8. A dental set plate assembly according to claim 1, wherein the product information indicia is in the form of a bar code.

9. A dental set plate assembly according to claim 1, wherein the hood includes two longitudinal side walls which at least substantially cover the relatively longer sides of the support body.

10. A dental set plate assembly according to claim 1, wherein the hood forms a hollow space above the mass which is of a height above the mass sufficient to permit clearance between all of the replacement teeth pressed into the mass and the hood yet less than twice the height of the replacement teeth above the mass.

11. A dental set plate assembly according to claim 1, wherein the support body is provided with a writing space, and the see through region of the hood extends horizontally over the replacement tooth in the dental set plate assembly and the writing space on the support body.

12. A dental set pirate assembly according to claim 1, wherein the product information indicia provides at least one of the type, dimension, color, material, and the fabricator of the replacement teeth in the dental set plate assembly.

13. A dental set plate assembly according to claim 1, wherein the mass is comprised of a selected one or wax, adhesive material, and soft plastic.

14. A dental set plate assembly for supporting therein a set of replacement teeth, comprising:
    support body having a channel and side walls;
    a deformable mass disposed in the channel of the support body, the mass releasably adhesively retaining a row of replacement teeth pressed thereinto;
    a non-opaque hood for covering the replacement teeth, the hood having walls;
    wherein the upper portion of the side walls of the support body are resiliently rearwardly movable and the resistance of the side wails to deflection substantially corresponds to the strength of the walls of the hood.

15. A dental set plate assembly for supporting therein a set of replacement teeth, comprising:
    support body having a channel and side walls;
    a deformable mass disposed in the channel of the support body, the mass releasably adhesively retaining a row of replacement teeth pressed thereinto;
    a non-opaque hood for covering the replacement teeth, the hood having a side wall,
    wherein the support body includes a grip recess and a side wall of the hood includes a cut out for permitting access to the grip recess when the hood is disposed on the support body.

* * * * *

UNITED STATES PATENT AND TRADEMARK OFFICE
CERTIFICATE OF CORRECTION

PATENT NO. : 6,758,670 B2
DATED : July 6, 2004
INVENTOR(S) : Andreas Eggler

It is certified that error appears in the above-identified patent and that said Letters Patent is hereby corrected as shown below:

Column 6,
Line 65, "or" should be -- of --; and "wail" should be -- wall --;

Column 7,
Line 1, "place" should be -- plate --;

Column 8,
Line 1, "tooth" should be -- teeth --;

Column 9,
Line 3, "pirate" should be -- plate --; and
Line 8, "or" should be -- of --.

Signed and Sealed this

Twenty-third Day of November, 2004

JON W. DUDAS
*Director of the United States Patent and Trademark Office*